(12) United States Patent
Bathelet

(10) Patent No.: US 9,599,574 B2
(45) Date of Patent: Mar. 21, 2017

(54) SYSTEM FOR INSPECTING A HOLLOW OBJECT THAT IS AT LEAST TRANSLUCENT, HAVING AT LEAST ONE MARKING

(71) Applicant: Guillaume Bathelet, Marcy l'étoile (FR)

(72) Inventor: Guillaume Bathelet, Marcy l'étoile (FR)

(*) Notice: Subject to any disclaimer, the term of this patent is extended or adjusted under 35 U.S.C. 154(b) by 0 days.

(21) Appl. No.: 14/902,222

(22) PCT Filed: Jul. 2, 2014

(86) PCT No.: PCT/FR2014/051695
§ 371 (c)(1),
(2) Date: Dec. 30, 2015

(87) PCT Pub. No.: WO2015/001255
PCT Pub. Date: Jan. 8, 2015

(65) Prior Publication Data
US 2016/0356726 A1    Dec. 8, 2016

(30) Foreign Application Priority Data

Jul. 2, 2013 (FR) ...................... 13 56466

(51) Int. Cl.
*G01N 21/00* (2006.01)
*G01N 21/90* (2006.01)
(Continued)

(52) U.S. Cl.
CPC ............. *G01N 21/90* (2013.01); *B07C 5/126* (2013.01); *B07C 5/3412* (2013.01);
(Continued)

(58) Field of Classification Search
CPC .... G01N 21/00; G01N 21/8851; G01N 21/90; B07C 5/126
(Continued)

(56) References Cited

U.S. PATENT DOCUMENTS

| 5,233,186 A | * | 8/1993 | Ringlien | G01N 21/90 250/223 B |
| 2011/0108627 A1 | * | 5/2011 | Bathelet | G06K 7/10732 235/454 |

FOREIGN PATENT DOCUMENTS

| DE | 19905135 C1 | 9/2000 |
| DE | 29920232 U1 | 12/2000 |
| EP | 2164028 A1 | 3/2010 |

OTHER PUBLICATIONS

French Search Report dated May 22, 2014 for French Application No. 1356466.
(Continued)

*Primary Examiner* — Roy M Punnoose
(74) *Attorney, Agent, or Firm* — Howard & Howard Attorneys PLLC

(57) ABSTRACT

A system for inspecting an object that is at least translucent extending along a vertical axis A, having at least one marking and being located in an inspection area including at least one inspection assembly that comprises a main illumination device positioned on one side of the inspection area, comprising a light source and emitting at least one light beam of illumination axis Δ. An acquisition device is positioned opposite the illumination device relative to the inspection area and comprising acquisition optics of optical axis Δ' and an image sensor optically aligned with the acquisition optics.

15 Claims, 3 Drawing Sheets

(51) Int. Cl.
B07C 5/34 (2006.01)
G06K 7/10 (2006.01)
B07C 5/12 (2006.01)
G01N 21/88 (2006.01)
G06K 7/14 (2006.01)

(52) U.S. Cl.
CPC ..... *G01N 21/8851* (2013.01); *G06K 7/10732* (2013.01); *G06K 7/10831* (2013.01); *G06K 7/10861* (2013.01); *G06K 7/1417* (2013.01)

(58) Field of Classification Search
USPC .......................................... 356/239.4, 240.1
See application file for complete search history.

(56) References Cited

OTHER PUBLICATIONS

International Search Report and Written Opinion of the International Searching Authority mailed Oct. 30, 2014 for PCT International Application No. PCT/FR2014/051695.

* cited by examiner

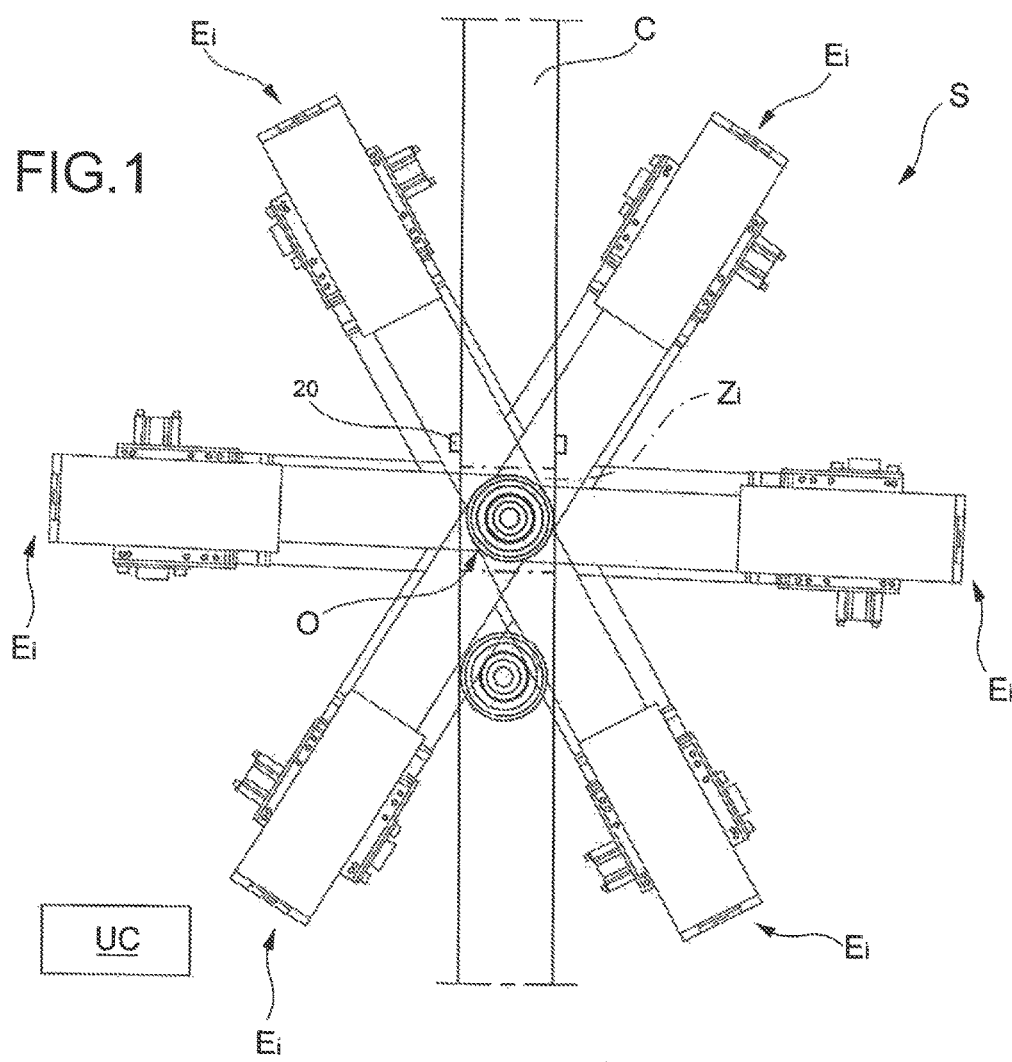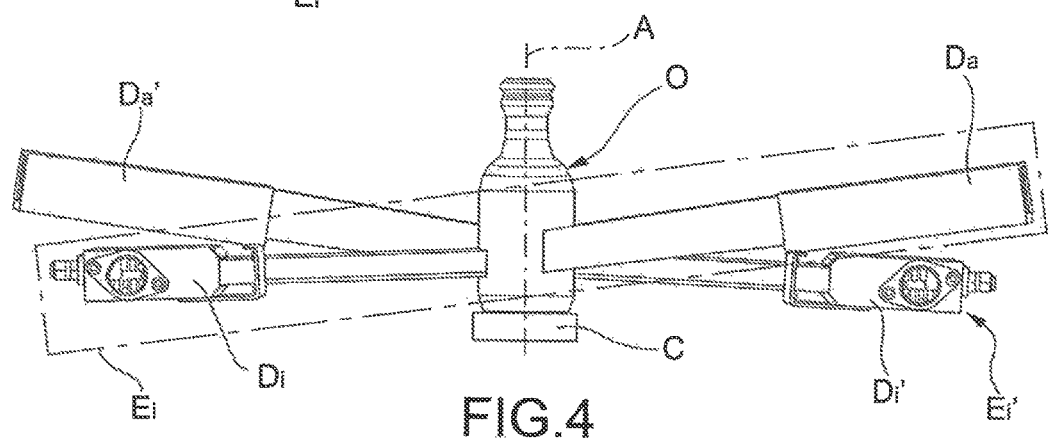

SYSTEM FOR INSPECTING A HOLLOW OBJECT THAT IS AT LEAST TRANSLUCENT, HAVING AT LEAST ONE MARKING

CROSS-REFERENCE TO RELATED APPLICATIONS

The present application is a National Stage of International Patent Application No. PCT/FR2014/051695, filed on Jul. 2, 2014, which claims priority to and all the benefits of French Patent Application No. 1356466 filed on Jul. 2, 2013, both of which are hereby expressly incorporated herein by reference in their entirety.

BACKGROUND OF THE INVENTION

1. Field of the Invention

The invention relates to the technical field of the inspection or scanning of a mark made in or on a transparent or translucent object. In one non-exclusive application, the invention relates to the scanning of two-dimensional codes such as Datamatrix codes etched or marked on the surface of receptacles or containers made of glass passing at a high speed in an in-line inspection system.

2. Description of the Related Art

Traceability in the glass industry is an increasingly strong constraint. Glass articles follow an increasingly complex manufacturing, distribution and filling process with numerous temporary storages and flow disruptions. Furthermore, the regulations stipulate having a capability to trace, through all the steps of manufacture, processing, distribution, routing of a food container by means of an identification enabling the traceability of the container. In order to meet this obligation, the glass industry has developed a hot marking technique making it possible to etch by means of a laser an individual identification mark specific to each container on a production line whereon the containers are produced at rates that may be between 50 and 600 articles per minute. The identification mark is presented for example in the form of a Datamatrix. In order to guarantee the effectiveness of such a traceability marking, it is necessary to ensure that the marking of each product is legible. For this purpose, it is necessary to scan the marking after the application thereof and cooling of the container at a rate compatible with the production rate so as not to create an accumulation point of the products and to be able, on one hand, to remove the containers wherein the marking is defective without delay and, on the other, record in a database the containers for which the marking is operational. The need for scanning at a high speed is also observed on filling lines in particular.

EP 2 164 028 discloses a system for inspecting code inscribed on the surface of glass receptacles intended for the pharmaceutical or chemical industry. As shown in FIGS. 5 and 6 of this published application, use is made therein of a point type lighting system focused on the code to be scanned so as to maximise the intensity of the signal received by the camera. The drawback of this optical system is that it is not suitable for compensating for the curvature of the glass surface. Indeed, if the code is situated on the edge of the glass article, the light will be deflected onto the sides and will escape the field of the camera. The usable inspection field is thus extremely limited to the centre of the product. Furthermore, the intensity of the signal received will be dependent on the angular position of the code in relation to the source and the acquisition device. Furthermore, the lighting system proposed is not suitable for adapting to different product diameters. Moreover, the optical system shown in FIG. 9a of the same document is an optical system with a single-lens camera. It collects all the reflective or incident rays in the lens without distinction.

As such, the inspection device disclosed in EP 2 164 028 is suitable for scanning code such as Datamatrix codes on good-quality glass intended for the fine chemical or pharmaceutical industries which has even wall thicknesses, smooth walls and no inclusion or surface defect. On the other hand, the device according to EP 2 164 028 is not suitable for scanning code on the surface of receptacles made of "rough" glass such as recycled glass used for the manufacture of food receptacles. Indeed, the inner and outer surfaces of such a receptacle may have numerous defects in respect of shape, glass distribution, inclusions in the glass matrix and skin liable to deflect the incident beam in the acquisition optics and generate a parasitic signal that the optical system according to EP 2 164 028 will not be able to filter. Similarly, glass skin defects such as wrinkling, seeding, grease stains may be superimposed on the signal within the code and will not be filtered by the optical system according to EP 2 164 028 rendering the code illegible.

SUMMARY OF THE INVENTION

The aim of the invention is to propose an acquisition system which is less or even not sensitive to these defects.

In order to meet these requirements, the invention relates to a system for inspecting an object that is at least translucent extending along a vertical axis A, having at least one marking and being located in an inspection area. The inspection system comprises:

at least one inspection assembly that comprises:
  a main illumination device positioned on one side of the inspection area, comprising a light source and emitting at least one light beam of illumination axis Δ,
  an acquisition device positioned opposite the illumination device relative to the inspection area and comprising acquisition optics of optical axis Δ' and an image sensor optically aligned with the acquisition optics.

According to the invention, for each inspection assembly, the acquisition optics comprise an entry lens and a secondary lens located between the entry lens and the image sensor, the entry lens being adapted to optically conjugate, in projection in a horizontal plane, the light source with the pupil of the secondary lens, the illumination axis Δ and the observation optical axis Δ' not being aligned or coplanar.

The conjugation carried out by the acquisition optics, and notably by the entry lens, makes it possible to ensure uniformity of the lighting perceived by the sensor. Furthermore, the illumination axis and the observation optical axis Δ' not being aligned, the rays of the illumination beam are, essentially, deflected in the presence of marking on the object to be inspected in the inspection area. Such an inspection by transmission deflectometry makes it possible to reduce the interference induced by the defects of the constituent material of the object during acquisition.

According to the invention, marking should be understood as any identification system suitable for being scanned in an automated manner such as in particular one or a plurality of one or two-dimensional barcodes, an alphanumeric code or a combination of both without this list being limiting or exhaustive.

According to one feature of the invention, for each inspection assembly, the illumination device and the acquisition device are adapted such that, in the absence of an object to be inspected in the inspection area, the light emitted by the illumination device does not reach the sensor of the acquisition device directly. This feature is intended to ensure that the inspection assembly operates in pure deflectometry.

According to a further feature of the invention, the illumination axis Δ and the optical axis Δ' form, in projection in a vertical plane V, a non-flat angle α and between 130° and 180°.

According to one feature of the invention, for each inspection assembly, the illumination axis Δ is substantially horizontal. As such, the illumination rays have an incidence substantially normal to the surface of the object to be observed in a part at least of the inspection area which makes it possible to increase the quantity of light passing through the object to be inspected to reach the marking which may be located on the face of the object situated opposite the illumination device.

According to one feature of the invention, for each inspection assembly, the illumination axis Δ is inclined relative to the horizontal. This feature makes it possible to limit the influence of the defects present on the face of the object facing each illumination device, notably in the case where the wall of the object to be inspected is substantially vertical.

According to a further feature of the invention, for each inspection assembly, the corresponding illumination device comprises an elongated light source which emits a light beam having an elongated brush shape extending along a substantially horizontal direction. Such a feature of the invention makes it possible to only illuminate the region, article or object to be inspected, wherein the marking to be scanned is supposed to be located such that the parasitic reflections and/or deflections induced by other regions of said object are limited as much as possible. This feature of the invention further makes it possible to correct the incidence of any curvature of the surface of the receptacle bearing the code to be scanned. According to one alternative embodiment of the invention, the light source forms a luminous line such that the light source can be described as a linear source. Preferably, this linear source has a horizontal longitudinal axis.

According to one alternative embodiment of this feature, for each inspection assembly, the corresponding elongated light source has a horizontal width greater than the height thereof. According to one embodiment of the invention, for each inspection assembly, the width of the light source is then greater than the largest horizontal dimension of the object to be inspected in the acquisition area. According to a further embodiment of the invention, the width of the light source is less than the largest horizontal dimension of the object to be inspected in the acquisition area. The width of the light source may then be substantially equal to the largest horizontal dimension of the object to be inspected in the acquisition area from which the thickness of the walls of the object to be inspected in the acquisition area has been subtracted.

In one preferred embodiment of the invention, the length of the linear source is adjustable so as to be able to be adapted to the dimensions of the object to be inspected.

According to one feature of the invention, for each inspection assembly, the main illumination device comprises telecentric illumination optics such that the rays of the light beam are substantially parallel with one another in the inspection area.

According to a further feature of the invention, each inspection assembly comprises a secondary illumination device located on the same side of the inspection area as the acquisition device. Such a secondary illumination device makes it possible to perform an observation in reflection.

According to an alternative embodiment of this feature, the secondary illumination device is positioned above the corresponding acquisition device. Such an arrangement makes it possible to reduce the size of each inspection assembly.

According to one embodiment, each acquisition device is adapted to observe an acquisition area which is located between two lower Pi and upper Ps horizontal acquisition planes located at a height Hi, or Hs, of a support plane PS of the object to be inspected in the inspection area and which has a vertically measured acquisition thickness Ea. The limited nature of the acquisition area relative to the whole object makes it possible to limit the inspection of the object to the sole region thereof where the marking to be scanned is supposed to be located. The thickness of the acquisition area and the height thereof are then chosen according to the dimensions of the marking and the position thereof accounting, on one hand, for the tolerances of the marking operation and, on the other, the high tolerances of the object in the inspection area.

According to one feature of this preferred embodiment, the acquisition device is located above the upper acquisition plane or below the lower acquisition plane. Such a set-up makes it possible to account for the geometry of the article inspected and the height of the mark, to facilitate the mechanical installation of the system according to the invention on either side of a system for conveying objects to be inspected in the inspection area, enabling the superimposition of an acquisition device and an illumination device.

According to a further feature of the preferred embodiment, the acquisition optics comprise an entry window of rectangular shape wherein the height Ha is greater than or equal to the acquisition thickness Ea and wherein the width La is less than or equal to the largest horizontal dimension of the objects to be inspected measured in the acquisition area. This feature makes it possible to limit the acquisition of the illumination light rays suitable for passing through the object to be inspected at the acquisition area.

According to a further feature of the preferred embodiment, the light beam from each illumination device has a vertically measured thickness Ei greater than the acquisition thickness Ea. This feature makes it possible to provide illumination of the acquisition area that is as homogeneous as possible.

According to a further feature of the preferred embodiment, each illumination device comprises an exit window of rectangular shape wherein the height Hi is greater than or equal to the acquisition thickness Ea and wherein the width Li is less than or equal to the largest horizontal dimension of the objects to be inspected measured in the acquisition area. This feature also makes it possible to provide illumination of the acquisition area that is as homogeneous as possible.

According to one feature of the invention, each illumination device comprises a convex exit dioptre which has a shape of a cylinder portion revolving about a horizontal axis. This shape of the exit dioptre makes it possible to define a pseudo-telecentric light source in the vertical plane which has a thickness greater than or equal to the marking height and for example substantially equal to the sum of the height of the marking, the position tolerances of the marking on the object and positioning tolerance of the object during the conveying thereof in the inspection area. This feature further makes it possible to ensure uniformity of the lighting perceived by the sensor. The set-up formed in this way is comparable to a Köhler light in the vertical plane. The source height is optimised and becomes comparable to the field diaphragm, the convex exit dioptre of the source is comparable to the condenser, the primary lens of the optical system is comparable to the lens of a microscope, the secondary lens of the optical system is comparable to an eyepiece.

According to the invention, the illumination optics may also be Fresnel lens type optics.

According to one feature of the invention, the entry and secondary lenses of the optical system are adapted to obtain a pericentric (hypercentric) or telecentric lens with respect to the surface to be inspected that is generally curved in the horizontal plane so as to increase the usable field of the system, the area of sharpness on the width of the curved field and limit the spherical aberrations on the field width.

As such, according to one feature of the invention, for each inspection assembly, the entry lens, the secondary lens and the distances between the lenses and the sensor are optimised to create a hypercentric or telecentric optical system so as to optimise the usable field width and the field depth in the horizontal plane at the inspection area.

According to a further feature of the invention, for each inspection assembly, the secondary lens of the acquisition optics comprises an adjustable diaphragm. The use of such a diaphragm makes it possible to limit the acceptance angle of the incident beams and check the contrast obtained at the acquisition device.

According to a further feature of the invention, the inspection system comprises at least four inspection assemblies arranged on either side of the inspection area and evenly distributed over 360°. This feature of the invention makes it possible to ensure satisfactory coverage of the acquisition making it possible to ensure that the marking to be scanned will be visualised by at least one inspection assembly. Preferably, the inspection system comprises six inspection assemblies wherein the acquisition fields overlap by a width greater than or equal to the width of a marking to be scanned.

According to one alternative feature, the inspection assemblies are distributed symmetrically on either side of a line for conveying objects to be inspected and are spaced so as to enable the passage of the objects to be inspected.

According to a further alternative embodiment of this feature, each illumination device of an inspection assembly is superimposed with an acquisition device with a further inspection assembly. This alternative embodiment makes it possible to optimise the size of the inspection system according to the invention while making it possible to distribute the inspection assemblies symmetrically on either side of a line for conveying objects to be inspected and are spaced so as to enable the passage of the objects to be inspected in the inspection area.

According to a further alternative embodiment of this feature, the acquisition system comprises a control unit that controls the inspection assemblies suitable for, on one hand, synchronise the operation of the illumination and acquisition devices of the same inspection assembly and, on the other, ensure operation at different times of each of the inspection assemblies.

According to a further alternative embodiment of this feature, the illumination devices are adapted to emit flashes of light of a duration less than or equal to the spatial resolution of the optical system divided by the movement speed of the articles on the conveyor. Such a flash of light makes it possible to perform an acquisition of an object located in the acquisition area without a risk of blurring.

According to a further alternative embodiment of this feature, the illumination devices are adapted to emit flashes of light of a duration less than or equal to the spatial resolution of the optical system divided by the movement speed of the articles on the conveyor and at a frequency greater than or equal to the movement speed of the articles on the conveyor divided by a fraction of the width of the marking to be analysed so as to make a plurality of images of the same marking. As such, it becomes possible to select the image which has the best contrast and/or the least defects, such as for example the mould seam line, which may give rise to interference/reflections in the image.

According to a further alternative embodiment of this feature, the illumination devices, acquisition devices and the control unit are adapted so that in a time interval less than or equal to the width, of a unitary element of the marking to be analysed, divided by the speed on the articles on the conveyor, each of the inspection assemblies has carried out at least one acquisition of the same object located in the acquisition or inspection area.

According to the invention, the control unit may also be adapted to provide simultaneous operation of all the inspection assemblies.

Obviously, the various features, alternative embodiments and embodiments of the inspection system according to the invention may be associated with one another according to various combinations provided that they are not incompatible or exclusive with respect to one another.

Moreover, various further features of the invention emerge from the description appended with reference to the drawings which illustrate a non-limiting embodiment of an inspection system according to the invention.

BRIEF DESCRIPTION OF THE DRAWINGS

FIG. 1 is a top view of the inspection system according to the invention.

FIG. 4 is a schematic elevation of two superimposed inspection assemblies constituting the system illustrated in FIG. 1.

DETAILED DESCRIPTION OF THE INVENTION

It should be noted that, in these figures, the structural and/or functional elements common to the various alternative embodiments may have the same references.

An inspection system according to the invention, as illustrated in FIG. 1 and designated overall by the reference S, is intended to enable automated inspection of the markings present on the surface of at least translucent objects such as glass bottles transiting in an inspection area Zi at high speeds of the order of 60 metres/minutes such that it passes of the order of 600 objects per minute in the inspection area. According to the example illustrated, the inspection area Zi corresponds to a portion of a conveyor C at which the inspection system S is arranged.

Figure 2:
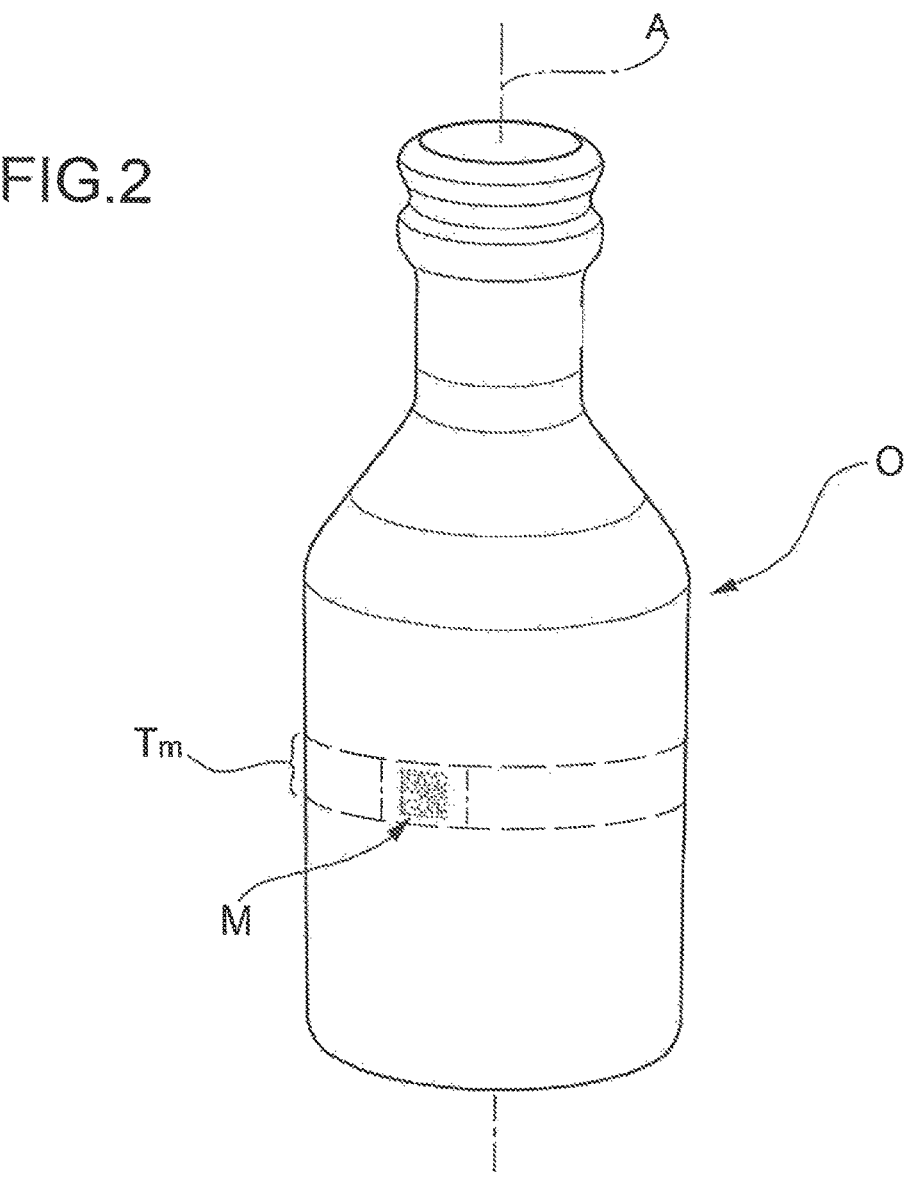
FIG. 2 is a schematic perspective view of an object including a marking to be scanned by the inspection system according to the invention.
Figure 3:
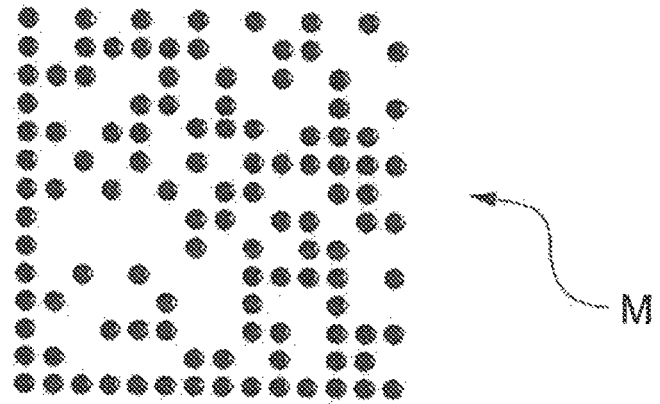
FIG. 3 is a larger-scale view of the marking of the object illustrated in FIG. 2.

In the present case and as shown in FIG. 2, each object to be inspected O is formed by a bottle extending along a vertical axis A and which has at the side thereof a marking M for example a high-density two-dimensional barcode also called Datamatrix seen more clearly in FIG. 3. The marking M occupies for example a square surface of 8 mm on the side. The marking M is made during the production process of the object O such that it is always located in the same region Rm thereof with a variability associated with the tolerances of the marking process. As such, the marking region Rm is inscribed in a section Tm of the peripheral wall of the object O. Moreover, the angular position of each object on the conveyor C is not known also the inspection system S is preferably in a position of being able to inspect the entire section Tm during the passage of each object in the inspection area Zi. This inspection may be made by applying to each object a rotational movement in the acquisition area Za. However, according to the example illustrated, the inspection system S is designed so as to be able to inspect the entire surface of the section Tm without applying a rotational movement on itself to the object O.

To this end, the inspection system S comprises at least four, and according to the example illustrated, six inspection assemblies Ei which are arranged on either side of the inspection area Zi without impeding the passage of the objects to be inspected on the conveyor C. The inspection assemblies Ei are distributed uniformly about the inspection area Zi so as to cover the 360° of the section Tm.

Each inspection assembly Ei comprises a main illumination device Di and an acquisition device Da as seen more particularly in FIG. 4 wherein two inspection assemblies Ei and Ei' can be seen. In order to optimise the size of the inspection system S, the main illumination device Di of the inspection assembly Ei is superimposed with the acquisition device Da' of the other inspection assembly Ei' as the acquisition device Da of the inspection assembly Ei is superimposed with the main illumination device Di' of the other inspection assembly Ei'. It is thus for the four other inspection assemblies, each acquisition device of an inspection assembly being superimposed with a main illumination device of another inspection assembly.

Figure 6:
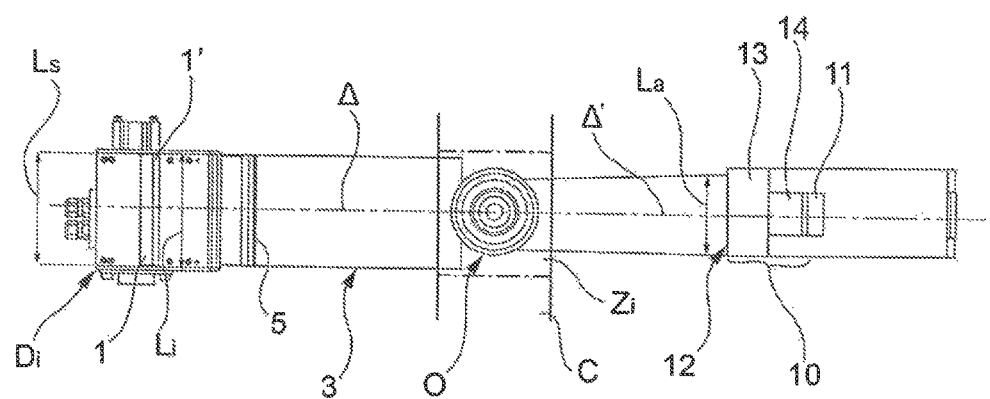
FIG. 6 is a top view of the inspection assembly represented in FIG. 5.
Figure 5:
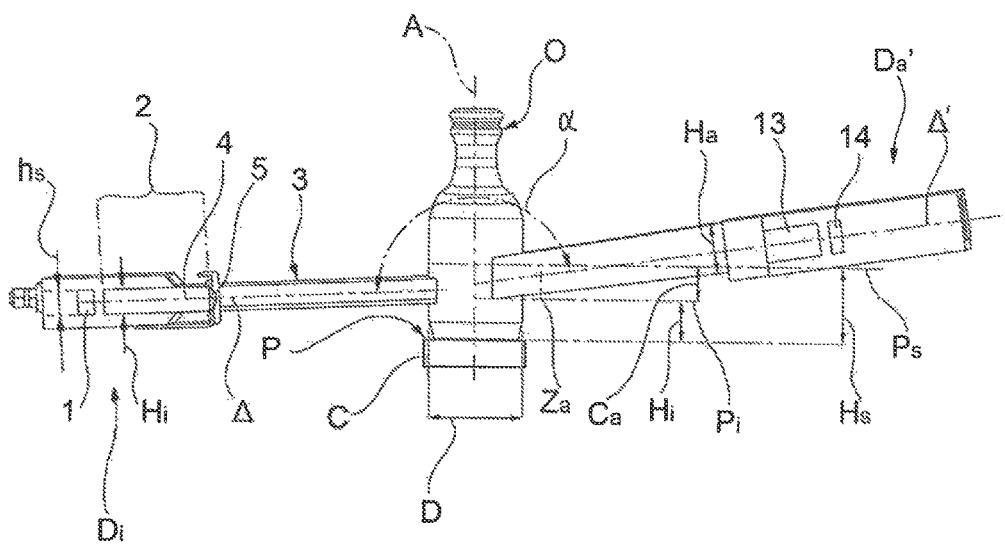
FIG. 5 is a schematic side-view elevation of an inspection assembly constituting the system illustrated in FIG. 1.

In order to simplify the description, the optical and functional features of the inspection assemblies will be described, relative to FIGS. 5 and 6, solely for the inspection assembly Ei. So as to render FIGS. 5 and 6 easier to read, only the corresponding main illumination device Di and acquisition device Da are represented therein. It should be understood that all the inspection assemblies Ei have substantially the same functional and optical features such that the quality of the images made is not dependent on the angular position of the object to be inspected in the inspection area Zi.

Each inspection assembly Ei thus comprises, on one hand, a main illumination device Di which is placed on one side of the inspection area Zi and, on the other, an acquisition device Da which is arranged opposite the illumination device Di relative to the inspection area Zi. The main illumination device Di and the acquisition device Da are then connected to a control unit UC adapted to control the operation thereof.

The illumination device Di comprises a light source 1 associated with illumination optics 2. According to the example illustrated, the light source 1 has an elongated shape and is formed by a horizontal row of light-emitting diodes 1' such that the light source 1 has a horizontal width Ls greater than the height hs thereof. The width Ls of the light source 1 is preferably greater than the largest horizontal dimension D of the object to be inspected O in the section Tm thereof In one embodiment, the length of the light source is controllable in such a way as to adapt same optimally to the object to be inspected and reduce as much as possible the influence of the lateral walls of the object to be inspected. Insofar as, according to the example illustrated, the light source is formed by a row of light-emitting diodes, it may then be described as pseudo-linear. Moreover, in order to act on the contrast obtained for scanning, it is possible to modulate the height hs of the light source. This modulation may notably be provided by the choice of light-emitting diodes. According to one alternative embodiment of the invention, a height-adjustable slot is used between the light source and the illumination optics, which offers the possibility of setting the contrast of the code and adjusting same according to the marking depth thereof to the limit of the contrast generated by the glass skin defects associated with the roughness and imperfection of the constituent matrix or material of the receptacle. The height setting of the light source is comparable to the aperture diaphragm in the vertical plane according to the Köhler lighting principle. The light source according to the invention is asymmetrical and can be considered as pseudo-point along the vertical axis and wide along the horizontal axis.

According to one alternative embodiment, oriented holographic diffusers are added between the light source and the illumination optics, the light source to adjust the contrast along both axes, vertical and horizontal.

The illumination optics 2 are associated with the light source 1 such that the illumination device Di emits a light beam 3 along an illumination axis Δ. The light beam 3 has, on a front view, an elongated brush shape, of rectangular cross-section, extending along a substantially horizontal direction. The illumination optics 2 are preferably telecentric or pseudo-telecentric such that the rays of the light beam 3 are substantially parallel with one another in the inspection area Zi and more particularly in the acquisition area Za which corresponds to a horizontal section of the inspection area Zi wherein the section Tm of the object to be inspected is inscribed where the mark M to be scanned or inspected is located. This telecentric or pseudo-telecentric property notably results from the fact that, in the present case, the illumination optics 4 have a convex exit dioptre 5 which is in the shape of a cylinder portion revolving about a horizontal axis.

The acquisition area Za is situated between two horizontal acquisition planes i.e. a lower acquisition plane Pi and an upper acquisition plane Ps which are located at a height Hi, or Hs of a support plane P, of the object O, defined by the conveyor C. The acquisition area Za then has a vertically measured acquisition thickness Ea equal to the difference between Hs and Hi. The thickness Ea is greater than or equal to the thickness of the section Tm and for example equal to the sum of the thickness of the section Tm and the vertical positioning tolerances of the object in the inspection area.

In order to limit the emission of parasitic rays by the illumination device Di, the latter comprises an exit window 4 of rectangular shape wherein the height Pi measured perpendicularly to the illumination axis Δ and, in the present case substantially vertically, and greater than or equal to the acquisition thickness Ea. The width Li of the exit window 4 is for its part greater than or equal to the largest horizontal dimension D of the object O in the acquisition area Za or in the section Tm.

The light beam 3 then has a thickness Ei substantially equal to the height Hi of the illumination window and a width Lf substantially equal to the width Li of the elimination window 4.

The light source 1 is controlled by the control unit UC and is adapted to be able to emit flashes of light of a duration between 10 μs and 1000 μs. Such a pulse duration makes it possible not to generate any blur when the acquisition device has a spatial resolution of 10 μm and the object O moves at a speed of 60 m/min in the inspection area. Furthermore, the light source is adapted to be capable of emitting flashes of light at a frequency greater than or equal to 1 kHz. Indeed, in the case of a rate of 600 articles/minute, the frequency of passage of the articles in the acquisition area is 10 Hz. For each article and for a marking of 8 mm, it is necessary to provide at least 3 flashes in the marking i.e. according to Shannon's theorem at least 6 periods and insofar as the conveying speed is 60 metres per minute, the calculation recommends a frequency of 750 Hz. As such, the light source may emit isolated flashes of light or, on the contrary, sequences of flashes.

The wavelength of the light emitted by the light source 1 is chosen according to the constituent material of the object O to be inspected and/or the content thereof. The light source 1 may have a fixed wavelength or colour or, on the other hand, a wavelength or colour controllable by the control unit UC so as to adapt to the object to be inspected O and/or the content thereof.

Each acquisition device Da comprises acquisition optics 10 having an optical axis Δ' and an image sensor 11 optically aligned with the acquisition optics 10. In order to operate in deflectometry, the illumination axis Δ and the optical axis Δ' form a non-flat obtuse angle between 130° and 180°. Furthermore, the illumination device Di and the corresponding acquisition device Da are arranged such that, in the absence of an object O in the inspection area Zi, the rays of the light beam 3 do not reach the acquisition optics 10 directly. In the present case, this result is achieved by positioning the acquisition device Da above the upper plane Ps defining the acquisition area Za. The same results could be achieved by positioning the acquisition device Da below the lower plane Pi defining the acquisition area Za.

Obviously, the acquisition device Da is adapted to be sensitive to the light emitted by the illumination device Di.

In order to limit the influence of parasitic lighting, the acquisition optics 10 comprise an entry window 12 of rectangular shape wherein the height Ha measured perpendicularly to the optical axis Δ' is greater than or equal to the acquisition thickness Ea of the acquisition area Za and wherein the width La is less than or equal to the largest horizontal dimension D of the object O in the acquisition area Za. The entry window is horizontally oriented such that the largest dimension thereof is substantially horizontal. It should be noted that, according to the invention, the optical system of each acquisition assembly is asymmetrical insofar as the exit window 4 and the entry window 12 each have a rectangular shape wherein the largest dimension is substantially horizontal.

According to the example illustrated, the acquisition optics 10 comprise an entry lens 13 and a secondary lens 14 located between the entry lens 13 and the image sensor 11. In the present case, the entry lens 13 is suitable for, in projection in a horizontal plane such as that in FIG. 6, conjugating the light source 3 viewed through the illumination optics 4 with the pupil 15 of the secondary lens 14. The acquisition optics may thus be described as a reimaging system.

The entry lens 13, the secondary lens 14, the distance of the image sensor 11 and the distance of the lens 13 relative to the surface of Tm are adapted to embody a telecentric or hypercentric optical system to maximise the width of the usable curved field and field depth according to the diameter D.

In one embodiment, the entry lens is asymmetrical so as to have a shape factor substantially equivalent to the entry window such that it is flat and it is possible to superimpose same with an illumination device.

Each of the acquisition Da and illumination Di devices of the six inspection assemblies Ei are connected to the control unit UC which is adapted to provide synchronised and sequential operation thereof according to the passage of the objects to be inspected in the inspection area Zi. As such, the inspection system comprises an optical barrier 20 which detects the entry of a new object O into the inspection area Zi.

The control unit UC is then adapted such that each of the six inspection assemblies Ei produces at least one image of each object O located in the inspection area. The control unit UC then provides sequential operation of the inspection assemblies Ei such that each successively produces an image of the object O, the six images having to be recorded in a time less than the residence time of the object in the inspection area Zi. For the production of each image, the illumination Di and acquisition Da devices of the same inspection assembly Ei have a synchronised operation whereas the other inspection assemblies are inactive. This procedure guarantees optimal illumination of the acquisition area. The acquisition and illumination devices are preferably adapted to enable the production of an image within a period less than or equal to the width of a marking to be analysed divided by the running speed of the articles on the conveyor.

Given the reactivity of the illumination Di and acquisition Da devices, the control unit UC may be adapted such that each of the inspection assemblies produces a plurality of images of the same object O located in the inspection area. It should be noted that, given the image capture rates, the position of the object may be considered to be stationary in the inspection area.

After acquisition of the images, the control unit UC is adapted to process the latter so as to identify therein any marking present and perform the scanning thereof. In the event of a valid reading, the object O is recorded as being conforming and in the event of an invalid reading, the control unit UC steers an evacuation of the object via a device located downstream from the inspection area and not shown in the figures.

The processing operations by the control unit UC of the images produced by the inspection assemblies of the system according to the invention are performed by algorithms well-known to those skilled in the art and not requiring more extensive description.

According to the example described above, the control unit is adapted to provided sequential operation of the inspection assemblies Ei; however, it could be adapted to provide simultaneous operation of the inspection assemblies wherein the illumination devices are activated at the same time and wherein the acquisition devices also operate substantially at the same time. Such simultaneous operation is enabled by the asymmetric optical design of the inspection assemblies Ei and by the use of the exit 4 and entry 12 windows which limit the parasitic lighting as much as possible.

Obviously, various alternative embodiments of the inspection system according to the invention may be envisaged within the scope of the appended claims. This invention has been described in an illustrative manner. It is to be understood that the terminology which has been used is intended to be in the nature of words of description rather than of limitation. Many modifications and variations of the invention are possible in light of the above teachings. Therefore, within the scope of the appended claims, the invention may be practiced other than as specifically described.

The invention claimed is:

1. A system for inspecting an at least translucent object extending along a vertical axis (A), having at least one marking (M) and being located in an inspection area (Zi), said inspection system comprising:
   at least one inspection assembly (Ei) that comprises
      a main illumination device (Di) positioned on one side of the inspection area (Zi), comprising a light source (S) and emitting at least one light beam of illumination axis ($\Delta$),
      an acquisition device (Da) positioned opposite the illumination device relative to the inspection area (Zi) and comprising acquisition optics of optical axis ($\Delta'$) and an image sensor optically aligned with the acquisition optics,
wherein for each inspection assembly (Ei), the acquisition optics comprise an entry lens and a secondary lens located between the entry lens and the image sensor, the entry lens being adapted to optically conjugate, in projection in a horizontal plane, the light source (S) with the pupil of the secondary lens, the illumination axis $\Delta$ and the observation optical axis $\Delta'$ not being aligned or coplanar.

2. The inspection system as set forth in claim 1, wherein, for each inspection assembly (Ei), the illumination axis $\Delta$ is substantially horizontal.

3. The inspection system as set forth in claim 1, wherein for each inspection assembly (Ei), the corresponding illumination device (Di) comprises an elongated light source (S) which emits a light beam having an elongated brush shape extending along a substantially horizontal direction.

4. The inspection system as set forth in claim 3, wherein, for each inspection assembly (Ei), the corresponding elongated light source (S) has a horizontal width greater than the height thereof, the width (Ls) of the light source (S) being greater than the largest horizontal dimension (D) of the object (O) to be inspected.

5. The inspection system as set forth in claim 1, wherein, for each inspection assembly (Ei), the main illumination device (Di) comprises telecentric illumination optics such that the rays of the light beam are substantially parallel with one another in the inspection area (Zi), the entry lens being adapted to optically conjugate, in projection in a horizontal plane, the light source (S) with the pupil of the secondary lens.

6. The inspection system as set forth in claim 1, wherein each acquisition device (Da) is adapted to observe an acquisition area (Za) which is located between two lower (Pi) and upper (Ps) horizontal acquisition planes located at a height (Hi), or (Hs), of a support plane (P) of the object to be inspected in the inspection area (Zi) and which has a vertically measured acquisition thickness (Ea).

7. The inspection system as set forth in claim 6, wherein the acquisition device (Da) is located above the upper acquisition plane or below the lower acquisition plane.

8. The inspection system as set forth in claim 6, wherein the acquisition optics comprise an entry window of rectangular shape wherein the height (Ha) is greater than or equal to the acquisition thickness (Ea) and wherein the width (La) is less than or equal to the largest horizontal dimension (D) of the objects (O) to be inspected measured in the acquisition area (Za).

9. The inspection system as set forth in claim 6, wherein the light beam (3) from each illumination device (Di) has a vertically measured thickness (Ei) greater than the acquisition thickness (Ea).

10. The inspection system as set forth in claims 6, wherein each illumination device (Di) comprises an exit window of rectangular shape wherein the height (Hi) is greater than or equal to the acquisition thickness (Ea) and wherein the width (Li) is less than or equal to the largest horizontal dimension of the objects to be inspected measured in the acquisition area (Za).

11. The inspection system as set forth in claim 1, wherein each illumination device (Di) comprises a convex exit dioptre which has a shape of a cylinder portion revolving about a horizontal axis.

12. The inspection system as set forth in claim 1, wherein, for each inspection assembly, the entry lens, the secondary lens and the distances between the lenses and the sensor are optimised to create a hypercentric or telecentric optical system so as to optimise the usable field width and the field depth in the horizontal plane at the inspection area.

13. The inspection system as set forth in claim 1, wherein it comprises at least four inspection assemblies (Ei) arranged on either side of the inspection area (Zi) and evenly distributed over 360°.

14. The inspection system as set forth in claim 13, wherein each illumination device (Di) of an inspection assembly (Ei) is superimposed with an acquisition device (Da) with a further inspection assembly (Ei).

15. The inspection system as set forth in claim 13, wherein it comprises a control unit (UC) adapted to control the inspection assemblies (Ei) and, on one hand, to synchronise the operation of the illumination (Di) and acquisition (Da) devices of the same inspection assembly (Ei) and, on the other, to ensure operation at different times of each of the inspection assemblies (Ei).

* * * * *